United States Patent [19]

Luce et al.

[11] Patent Number: 4,506,226

[45] Date of Patent: Mar. 19, 1985

[54] ION CONCENTRATION MONITOR

[75] Inventors: Robert S. Luce, Los Altos; Ross A. Quinn, Los Altos Hills, both of Calif.

[73] Assignee: Lockheed Missiles & Space Company, Inc., Sunnyvale, Calif.

[21] Appl. No.: 379,650

[22] Filed: May 19, 1982

[51] Int. Cl.³ .............................................. G01N 27/62
[52] U.S. Cl. .................................. 324/459; 324/438; 324/425; 204/406
[58] Field of Search ............... 324/438, 450, 459, 425, 324/434, 444, 449, 71.1, 439; 204/406, 412, 416

[56] References Cited

U.S. PATENT DOCUMENTS

| | | | |
|---|---|---|---|
| 3,648,159 | 3/1972 | Stansell et al. | 324/438 |
| 3,696,019 | 10/1972 | Arrington et al. | 324/425 |
| 3,855,101 | 12/1974 | Wilson | 324/425 |
| 4,060,717 | 11/1977 | Sitek | 324/71.1 |

Primary Examiner—Michael J. Tokar
Assistant Examiner—Kevin D. O'Shea
Attorney, Agent, or Firm—John J. Morrissey

[57] ABSTRACT

An apparatus for monitoring ion concentrations in an aqueous solution comprises a plurality of electrodes insertable into the solution. At least two of the electrodes are ion-selective for particular ions. Each ion-selective electrode is electrically connected to a corresponding impedance buffer, which generates a low-impedance output signal having the same voltage as the electode. A plurality of operational amplifiers in full differential configuration is provided, each operational amplifier receiving a particular pair of output signals generated by the impedance buffers. Each differential amplifier generates an output signal indicating the potential difference between the impedance buffer output signals received as inputs by the differential amplifier.

6 Claims, 2 Drawing Figures

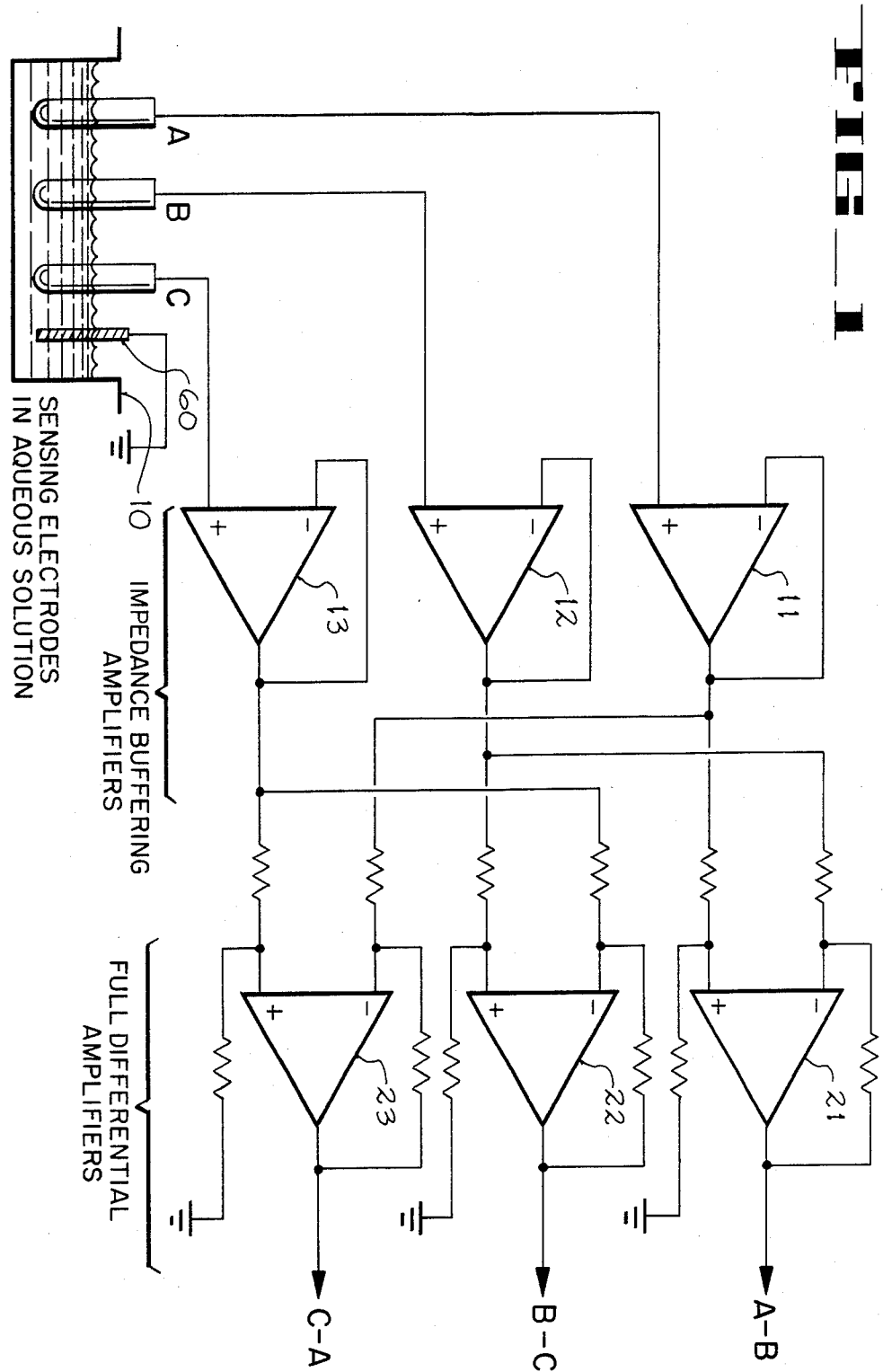

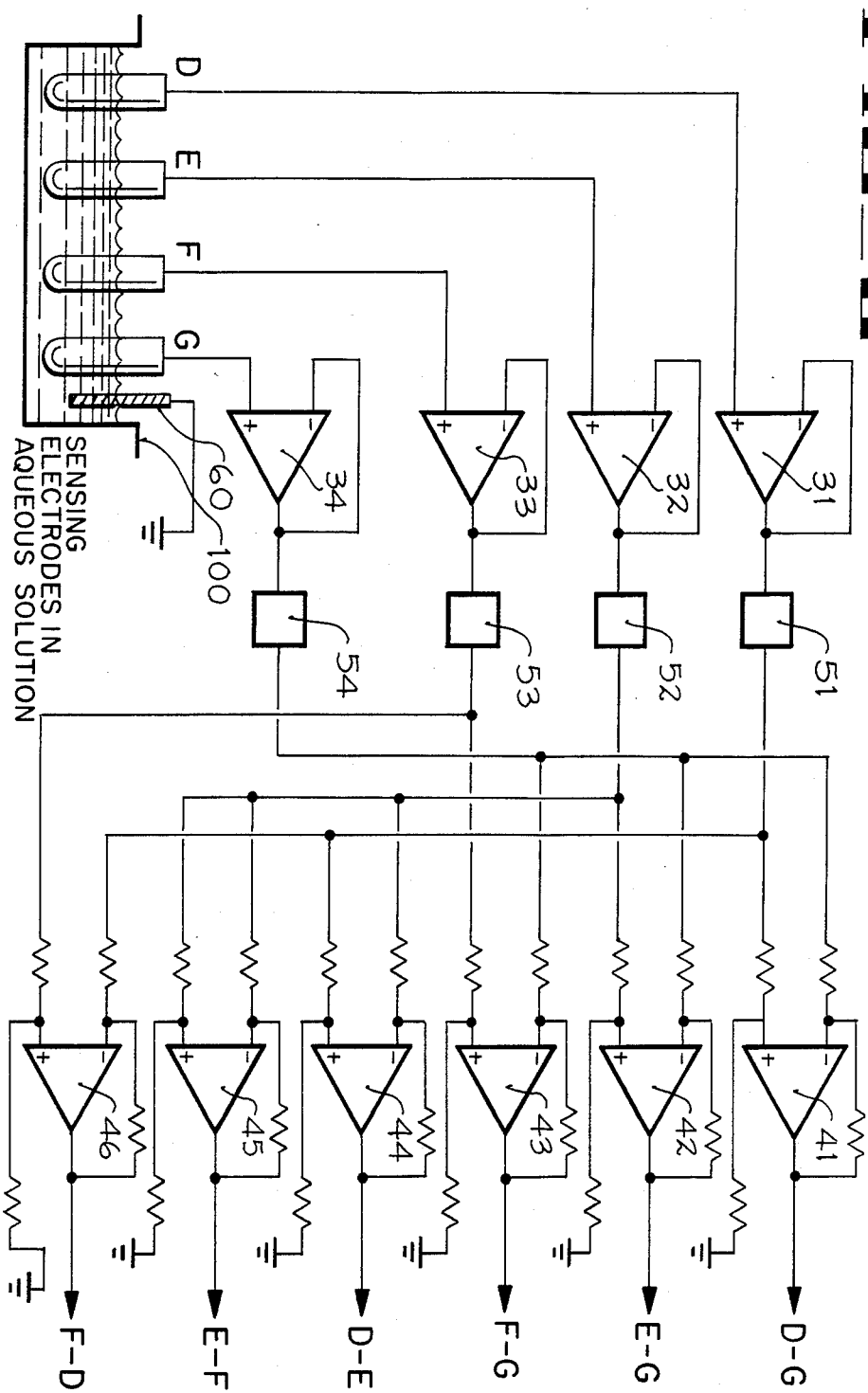
FIG_2

ION CONCENTRATION MONITOR

TECHNICAL FIELD

This invention relates to apparatus for measuring ion concentration in aqueous solution.

DESCRIPTION OF THE PRIOR ART

Conventionally, concentration of a particular ion in aqueous solution was determined by measuring difference of electrical potential between a reference electrode and an ion-selective electrode immersed in the solution. Where the concentrations of two or more ions in aqueous solution were to be determined simultaneously, it was necessary to provide a pair of electrodes, viz., a reference electrode and an ion-selective electrode, for each ion whose concentration was to be determined.

In the prior art, it was not possible to use a common reference electrode for a plurality of ion-selective electrodes to determine concentrations simultaneously for two or more ions in an aqueous solution.

SUMMARY OF THE INVENTION

It is an object of the present invention to provide apparatus for determining concentrations of two or more ions in an aqueous solution simultaneously, using a common reference electrode electrically referred to a plurality of electrodes that are ion-selective for the particular ions whose concentrations are to be determined.

It is also an object of the present invention to provide apparatus capable of generating differential voltage measurements between pairs of ion-selective electrodes chosen from among a plurality of ion-selective electrodes immersed in an aqueous solution. In accordance with the present invention, any one of the ion-selective electrodes can function as a "reference" electrode with respect to which differential voltage measurements can be made and cross-checking on the functioning of the individual electrodes can be performed.

An apparatus in accordance withthe present invention, which was developed in response to an industrial ion concentration monitoring requirement, comprises at least three electrodes, at least two of which are ion-selective. Each ion-selective electrode is electrically connected to a corresponding impedance buffer, which generates a buffered output signal having the same voltage as the electrode. A plurality of operational amplifiers in full differential configuration is provided, each operational amplifier being disposed to receive the buffered output signals generated by a particular pair of impedance buffers. The total number of differential amplifiers is such that each pair of buffered output signals can be received as inputs to a corresponding one of the differential amplifiers. Each differential amplifier generates an output signal indicating the potential difference between the pair of impedance buffer output signals received as inputs by the differential amplifier.

DESCRIPTION OF THE DRAWING

FIG. 1 is a schematic representation of an ion concentration monitor in accordance with the present invention, in which three ion-selective electrodes are utilized.

FIG. 2 is a schematic representation of an ion concentration monitor in accordance with the present invention, in which three ion-selective electrodes in combination with a reference junction electrode are utilized.

BEST MODE OF CARRYING OUT THE INVENTION

As illustrated in FIG. 1, ion-selective electrodes A, B and C are shown immersed in a vessel 10 containing an aqueous solution. Ion-selective electrodes are commercially available items advertized in, e.g., the sales catalog published by Markson Science, Inc., of Del Mar, Calif. Electrode A might be, e.g., a pH sensing electrode (i.e., an $H^{30}$ selective electrode); electrode B might be, e.g., an $Na+$ selective electrode; and electrode C might be, e.g., an $F^-$ selective electrode.

Ion-selective electrodes typically have extremely high electrical impedances (on the order of 100 megohms). In order to convert electrode impedances to tractable values, electrodes A, B and C are connected to corresponding integrated circuit operational amplifiers 11, 12 and 13, respectively, which function as impedance buffering amplifiers. The amplifiers 11, 12 and 13, which have field effect transisitor (FET) inputs, are configured as high-input impedance, unity gain, voltage followers. A Series 3528 FET operational amplifier marketed by Burr-Brown Research Corporation of Tucson, Ariz., has been found to function satisfactorily for this purpose.

The outputs of the impedance buffering amplifiers 11, 12 and 13 are differentially amplified by integrated circuit operational amplifiers 21, 22 and 23, which are configured by means of external resistors as full differential, unity gain amplifiers. More particularly, the output of the impedance buffering amplifier 11 serves as input to the differential amplifiers 21 and 23; the output of the impedance buffering amplifier 12 serves as input to the differential amplifiers 21 and 22; and the output of the impedance buffering amplifier 13 serves as input to the differential amplifiers 22 and 23. An LM741C operational amplifier marketed by National Semiconductor Corporation of Santa Clara, Calif., has been found to function satisfactorily for this purpose. Functional items such as power supplies, frequency compensating capacitors and offset nulling potentiometers, whose utility would be apparent to a worker skilled in the art upon studying FIG. 1, are not shown in the drawing.

The output of the differential amplifier 21 is a differential voltage measurement indicating the difference of electrical potential between electrodes A and B. Similarly, the output of the differential amplifier 22 is a differential voltage measurement indicating the difference of electrical potential between electrodes B and C; and the output of the differential amplifier 23 is a differential voltage measurement indicating the difference of electrical potential between electrodes C and A.

A particularly suitable configuration of the present invention for application in industrial process control is illustrated in FIG. 2, in which electrodes D, E, F and G are shown immersed in vessel 100 containing an aqueous solution. The electrodes D, E and F are ion-selective electrodes, such as pH sensing, $Na+$ sensing and $F^-$ sensing electrodes, respectively. Electrode G is a reference electrode, e.g., a reference junction electrode. Electrode D is connected to impedance buffering amplifier 31; electrode E is connected to impedance buffering amplifier 32; electrode F is connected to impedance buffering amplifier 33; and electrode G is connected to impedance buffering amplifier 34. The impedance buffering amplifiers 31, 32, 33 and 34 generate signals that are low-impedance equivalents of the voltages at the electrodes D, E, F and G, respectively.

The outputs from the impedance buffering amplifiers 31, 32, 33 and 34 and differentially amplified by operational amplifiers 41, 42, 43, 44, 45 and 46, which are configured by means of external resistors as full differential, unity gain amplifiers. The type of apparatus described in FIG. 2 could in principle be modified for use with any number n of electrodes, where n>3. For n electrodes, there would be n corresponding impedance buffering amplifiers. The total number of differential amplifiers needed would be such that each possible pair of buffered output signals from the n impedance buffering amplifiers could be received as input to a particular one of the differential amplifiers. In general, the number of differential amplifiers needed to accommodate n impedance buffering amplifiers is $(n^2-n)/2$, where n>3. Thus, where n=4, as shown in FIG. 2, the number of differential amplifiers is 6.

In FIG. 2 the output of the impedance buffering amplifier 31 serves as input to the differential amplifiers 41, 44 and 46. The output of the impedance buffering amplifier 32 serves as input to the differential amplifiers 42, 44 and 45. The output of the impedance buffering amplifier 33 serves as input to the differential amplifiers 43, 45 and 46. The output of the impedance buffering amplitude 34 serves as input to the differential amplifiers 41, 42 and 43.

The output of the differential amplifier 41 is a differential voltage measurement indicating the difference of electrical potential between electrodes D and G. Similarly, the output of the differential amplifier 42 is a differential voltage measurement indicating the difference of electrical potential between the electrodes E and G; the output of the differential amplifier 43 is a differential voltage measurement indicating the difference of electrical potential between the electrodes F and G; and the output of the differential amplifier 44 is a differential voltage measurement indicating the difference of electrical potential between the electrodes D and E. The output of the differential amplifier 45 is a differential voltage measurement indicating the difference of electrical potential between the electrodes E and F; and the output of the differential amplifier 46 is a differential voltage measurement indicating the difference of electrical potential between the electrodes F and D.

As shown in FIG. 2, corresponding isolation amplifier modules 51, 52, 53 and 54 could be provided following the impedance buffering amplifiers 31, 32, 33 and 34 to provide full electrical isolation between the aqueous solution and the output circuitry. A Model 290A isolation amplifier marketed by Analog Devices, Inc., of Norwood, Mass., has been found to function satisfactorily for this purpose.

In order to remove stray electical charge, a small chemically inert metal rod 60 inserted into the aqueous solution could be connected to "signal ground" of the electronic circuitry to act as a grounding electrode for the solution.

Various embodiments have been described herein for an ion concentration monitor in accordance with the present invention. Other embodiments suitable for particular applications would become apparent to workers skilled in the art upon perusal of the foregoing specification and accompanying drawing. Thus, the description presented herein is to be understood as illustrative of the invention. The invention is more generally defined by the following claims and their equivalents.

We claim:

1. An apparatus for simultaneously monitoring ion concentrations for a plurality of different ions in an aqueous solution, said apparatus comprising:
   (a) at least three electrodes insertable into said solution, at least two of said electrodes being ion-selective for particular ions;
   (b) at least three electrical impedance bufers, each one of said electrodes being electrically connected to a corresponding one of said electrical impedance buffers, each electrical impedance buffer generating an electrical signal indicative of electrical potential on the electrode to which the corresponding impedance buffer is connected; and
   (c) a plurality of operational amplifiers disposed in full differential configuration, each differential operational amplifier being connected to receive inputs from a corresponding pair of said impedance buffers, each differential operational amplifier generating a signal indicative of electrical potential difference between a corresponding pair of said electrodes so that the electical potential difference between any pair of ion-selective electrodes can be monitored, all of said differential operational amplifiers generating said signals simultaneously.

2. The ion concentration monitoring apparatus of claim 1 wherein one of said electrodes is a reference junction electrode.

3. The ion concentration monitoring apparatus of claim 1 wherein each of said fimpedance buffers is configured as a high-input impedance, unity gain voltage follower.

4. The ion concentration monitoring apparatus of claim 1 wherein each of said differential operational amplifiers is configured by means of external resistors as a full differential, unity gain amplifier.

5. The ion concentration monitoring apparatus of claim 1 wherein a corresponding isolation amplifier module is electrically connected between each impedance buffer and the differential operational amplifiers receiving the output of the impedance buffer.

6. The ion concentration monitoring apparatus of claim 1 further comprising a chemically inert metallic structure insertable into said solution and connectable to signal ground.

* * * * *